United States Patent [19]
Karasiewicz et al.

[11] Patent Number: 5,382,657
[45] Date of Patent: Jan. 17, 1995

[54] PEG-INTERFERON CONJUGATES

[75] Inventors: Robert Karasiewicz, Parsippany; Carlo Nalin, Franklin Lakes; Perry Rosen, North Caldwell, all of N.J.

[73] Assignee: Hoffmann-La Roche Inc., Nutley, N.J.

[21] Appl. No.: 935,770

[22] Filed: Aug. 26, 1992

[51] Int. Cl.⁶ .................... C07D 213/89; C07K 3/08; C07K 15/26
[52] U.S. Cl. .................. 530/351; 424/85.4; 424/85.7; 530/409; 530/410; 546/300; 546/301; 558/276
[58] Field of Search ............ 546/261, 300, 301; 530/410, 409, 406, 405, 351; 568/672; 424/85.4, 85.5, 85.6, 85.7; 558/276

[56] References Cited

U.S. PATENT DOCUMENTS

| | | | |
|---|---|---|---|
| 2,651,657 | 9/1953 | Mikeska et al. | 558/276 |
| 3,607,653 | 9/1971 | Ziffer et al. | 435/188 |
| 3,619,371 | 11/1971 | Crook et al. | 435/179 |
| 3,632,828 | 1/1972 | Frevel et al. | 558/276 |
| 3,639,213 | 2/1972 | Ginger et al. | 435/178 |
| 3,645,852 | 2/1972 | Axen et al. | 435/181 |
| 3,788,948 | 1/1974 | Kagedal et al. | 435/180 |
| 3,959,080 | 5/1976 | Orth et al. | 435/179 |
| 4,002,531 | 1/1977 | Royer | 435/188 |
| 4,094,744 | 6/1978 | Hartdegen et al. | 530/816 |
| 4,100,271 | 7/1978 | Krezanoski | 514/11 |
| 4,179,337 | 12/1979 | Davis et al. | 435/181 |
| 4,261,973 | 4/1981 | Lee et al. | 424/78.3 |

(List continued on next page.)

FOREIGN PATENT DOCUMENTS

| | | |
|---|---|---|
| 0154316 | 9/1985 | European Pat. Off. . |
| 304311 | 2/1989 | European Pat. Off. . |
| 87/00056 | 1/1987 | WIPO . |
| 6546 | 7/1989 | WIPO . |
| 4606 | 5/1990 | WIPO . |
| 5534 | 5/1990 | WIPO . |
| 7938 | 7/1990 | WIPO . |
| 90/13540 | 11/1990 | WIPO . |
| 7190 | 5/1991 | WIPO . |
| 8229 | 6/1991 | WIPO . |

OTHER PUBLICATIONS

Veronese, Applied Biochem. & Biotechnolo. 11;141–152 (1985).
Arend et al., J. Clin. Invest. 88:1694–1697 (1990).
Knauf et al., J. Biological. Chem. 263:15064–15070 (1988).
Ho et al., Drug Metab. and Disposition 14:349–352 (1986).
King et al., Int. Archs. Allergy Appl. Immun. 66:439–446 (1981).
Nureddin et al., Biochem. J. 147:71–81 (1975).
Abuchoski et al., Biochem. Biophys. 7:175–186 (1984).
Eisenberg et al., Nature 343:341–346 (1990).
Ohlsson et al., Nature 348:550–552 (1990).
Szego et al., Chem. Abs. 101:700 Abstract No. 130594 (1984).
King et al., Int. J. Protein Peptide Res. 16:147p14 155 (1980).

*Primary Examiner*—Jeffrey E. Russel
*Attorney, Agent, or Firm*—George M. Gould; William H. Epstein; Catherine R. Roseman

[57] ABSTRACT

Substituted PEG-interferon conjugates of formulae IA and IB where PEG is linked by means of activated linking reagents of formulae IIA, IIB, or IIB-1 to an amino group in the interferon, and activated linking reagents of formulae IIA, IIB, or IIB-1. The conjugates are not readily susceptible to in vivo hydrolytic cleavage, have enhanced in vivo half life, and reduce the immunogenicity of the interferon while maintaining biological activity.

20 Claims, 3 Drawing Sheets

U.S. PATENT DOCUMENTS

| | | | |
|---|---|---|---|
| 4,275,000 | 6/1981 | Ross | 435/188 |
| 4,301,144 | 11/1981 | Iwashita et al. | 514/6 |
| 4,310,397 | 1/1982 | Kaetsu et al. | 522/173 |
| 4,486,344 | 12/1984 | Buckler | 530/809 |
| 4,496,689 | 1/1985 | Mitra | 435/178 |
| 4,609,546 | 9/1986 | Hirotani | 530/351 |
| 4,640,835 | 2/1987 | Shimizu et al. | 435/212 |
| 4,704,274 | 11/1987 | Sakuma et al. | 530/413 |
| 4,732,863 | 3/1988 | Tomasi et al. | 436/547 |
| 4,766,106 | 8/1988 | Katre et al. | 514/12 |
| 4,791,192 | 12/1988 | Nakagawa et al. | 530/399 |
| 4,810,638 | 3/1989 | Albarella et al. | 530/408 |
| 4,818,769 | 4/1989 | Nunberg et al. | 514/2 |
| 4,847,079 | 7/1989 | Kwan | 424/85.7 |
| 4,851,220 | 7/1989 | Yim et al. | 424/85.7 |
| 4,871,538 | 10/1989 | Yim et al. | 424/85.7 |
| 4,894,226 | 1/1990 | Aldwin et al. | 424/85.2 |
| 4,902,502 | 2/1990 | Nitecki et al. | 530/351 |
| 4,917,888 | 4/1990 | Katre et al. | 514/12 |
| 4,935,465 | 6/1990 | Garman | 530/402 |
| 5,100,664 | 3/1992 | Doyle et al. | 424/92 |
| 5,102,872 | 4/1992 | Singh et al. | 514/21 |
| 5,122,614 | 6/1992 | Zalipsky | 435/188 |
| 5,281,698 | 1/1994 | Nitecki | 530/409 |

PEG-INTERFERON CONJUGATES group in the interferon (IFN) to PEG. The present invention is directed to physiologically active conjugates having the formulae:

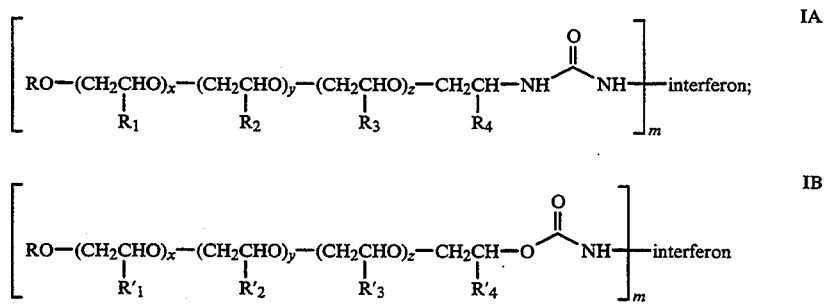

BACKGROUND OF THE INVENTION

Various natural and recombinant proteins have medical and pharmaceutical utility. Once they have been purified, separated, and formulated, they can be parenterally administered for various therapeutic indications. However, parenterally administered proteins may be immunogenic, may be relatively water insoluble, and may have a short pharmacological half life. Consequently, it can be difficult to achieve therapeutically useful blood levels of the proteins in patients.

These problems may be overcome by conjugating the proteins to polymers such as polyethylene glycol. Davis et al., U.S. Pat. No. 4,179,337 disclose conjugating polyethylene glycol (PEG) to proteins such as enzymes and insulin in order to result in conjugates where the protein would be less immunogenic and would retain a substantial proportion of its physiological activity. Nakagawa, et al. disclose conjugating PEG to islet-activating protein to reduce its side-effects and immunogenicity. Veronese et al., Applied Biochem. and Biotech, 11:141–152 (1985) disclose activating polyethylene glycols with phenyl chloroformates to modify a ribonuclease and a superoxide dimutase. Katre et al. U.S. Pat. Nos. 4,766,106 and 4,917,888 also disclose solubilizing proteins by polymer conjugation. PEG and other polymers are conjugated to recombinant proteins to reduce immunogenicity and increase half-life. See Nitecki, et al., U.S. Pat. No. 4,902,502, Enzon, Inc., International Application No. PCT/US90/03133, Nishimura et al., European Patent Application 154,316 and Tomasi, International Application Number PCT/US85/02572.

Previous methods of forming PEG/protein conjugates and the conjugates which result from said methods present several problems. Among these problems is that certain methods of forming these protein-PEG conjugates may inactivate the protein so that the resulting conjugates may have poor biological activity. In addition, certain linkers utilized in forming these PEG-protein conjugates may be susceptible to in vivo hydrolytic cleavage. When such cleavage occurs after administration, these conjugates lose the beneficial properties provided by PEG.

SUMMARY OF THE INVENTION

The invention discloses novel interferon-PEG conjugates with unique linkers which connect an amino wherein R is lower alkyl; $R_1$, $R_2$, $R_3$, $R_4$, $R'_1$, $R'_2$, $R'_3$, and $R'_4$ are H or lower alkyl; m is a number up to the number of accessible amino groups in the protein and x, y and z are selected from any combination of numbers such that the conjugate has at least a portion of the biological activity of the protein which forms the conjugate; with the proviso that at least one of $R_1$, $R_2$, $R_3$, and $R_4$ is lower alkyl.

DETAILED DESCRIPTION OF THE INVENTION

Figure 1:
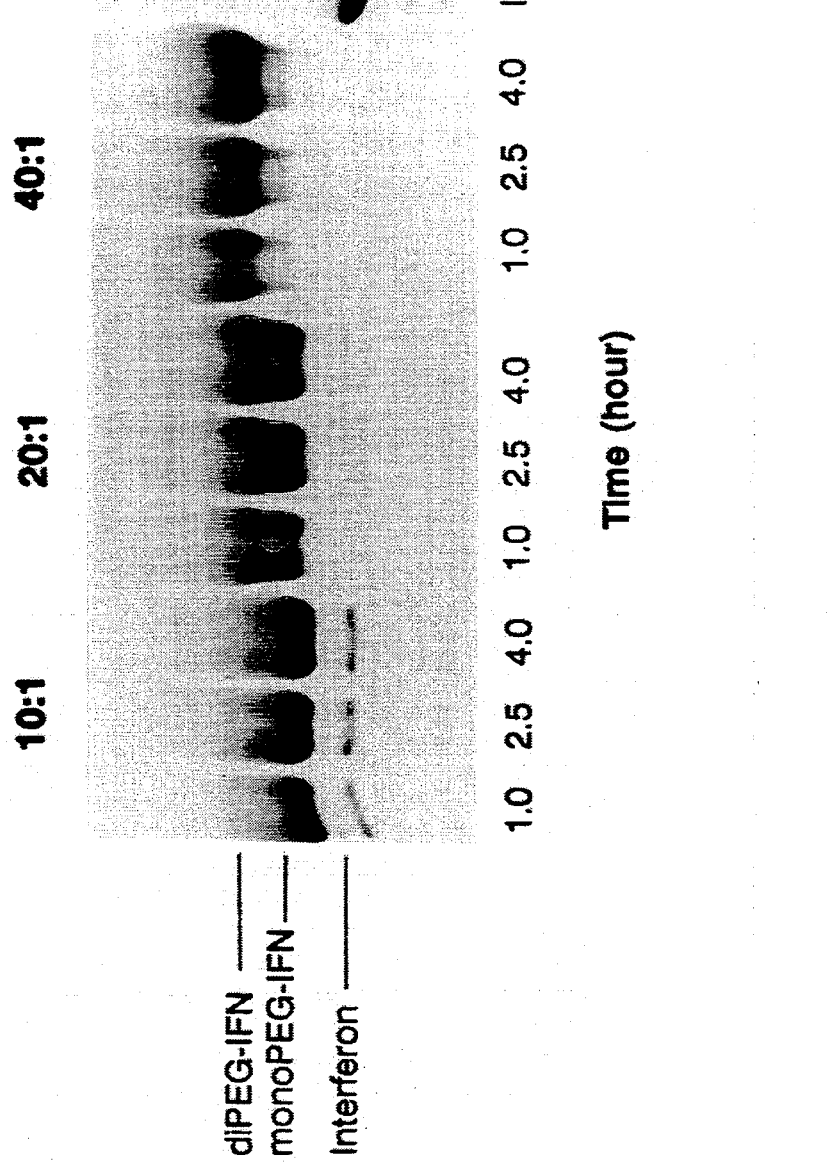
FIG. 1: Time course of PEG modification with the compound of Example 7. Interferon (5 mg/ml) was incubated with 10-fold, 20-fold, or 40-fold excess of reagent to protein for the times indicated in 25 mM Tricine (pH 10.0), 0.5M KSCN, 100 mM NaCl. Aliquots were removed at various times, quenched with glycine and analyzed on a 15% SDS-PAGE gel. On the label "I" is for interferon.
Figure 2:
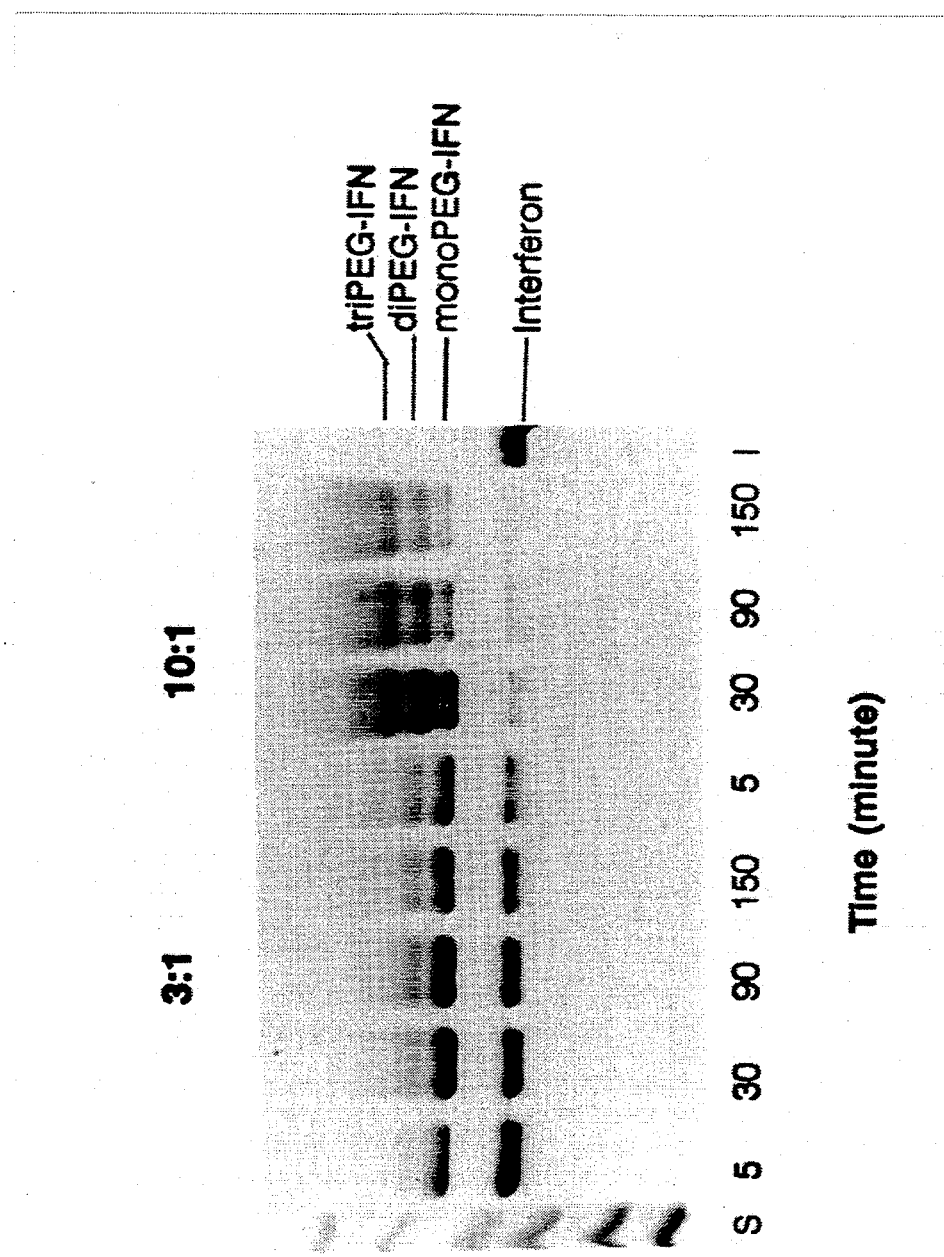
FIG. 2: Time course of PEG modification with the compound of Example 5. Interferon was incubated with a 3-fold or 10-fold excess of reagent for the indicated times as in FIG. 1. At the times indicated, aliquots were removed, quenched with glycine, and analyzed on a 15% SDS-PAGE gel. "S" is the label for protein molecular weight standards, "I" is the label for interferon.
Figure 3:
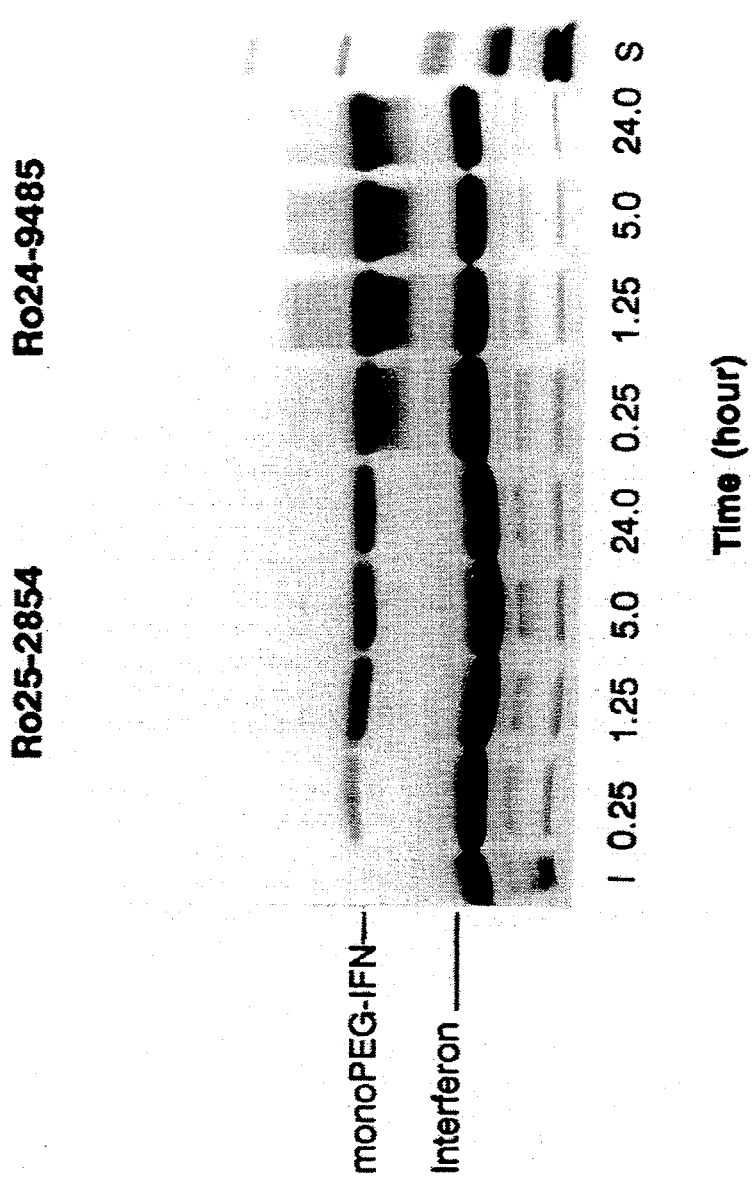
FIG. 3: Comparison of PEG modification with the compound of Example 1, and of Example 3. Interferon was incubated with a 3-fold excess of each reagent for 0.25, 1.5 or 24 hours. Aliquots were removed, quenched with glycine and analyzed on a 15% SDS-PAGE gel. "S" is the label for protein molecular weight standards, "I" is the label for interferon.

In accordance with this invention, the IFN conjugates of formulae IA and IB are produced by condensing activated PEG where a terminal hydroxy or amino group has been replaced by an activated linker. These reagents can then react with one or more of the free amino groups in the IFN. Condensation with only one amino group to form a monoPEGylated conjugate is a feature of this invention. The novel activated reagents used to produce the conjugates have the following formulae:

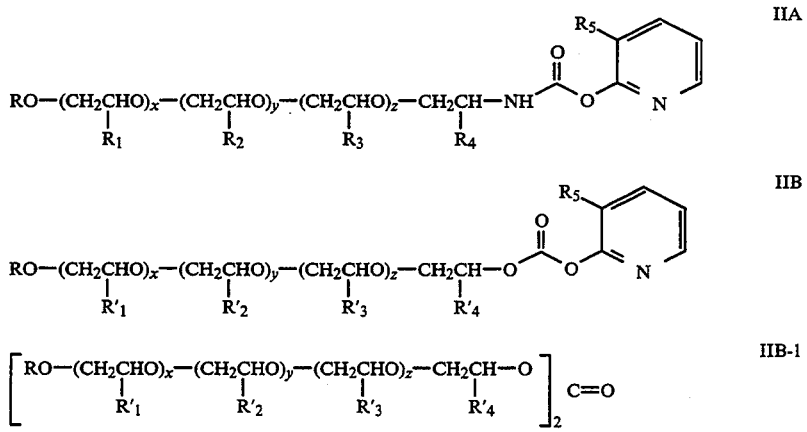

$$\text{IIA}$$
$$\text{IIB}$$
$$\text{IIB-1}$$

wherein R, R$_1$, R$_2$, R$_3$, R$_4$, R'$_1$, R'$_2$, R'$_3$, and R'$_4$ are as above; R$_5$ is H or lower alkyl; and x, y, and z are selected from any combination of numbers such that the polymer when conjugated to a protein allows the protein to retain at least a portion of the activity level of its biological activity when not conjugated; with the proviso that at least one of R$_1$, R$_2$, R$_3$, and R$_4$ is lower alkyl.

In accordance with this invention, by using the activated PEG reagents of formula IIA, IIB, or IIB-1 to produce the conjugates, a linking bond between the free amino groups in a protein such as interferon (IFN) and the PEG is formed so that the resulting conjugate retains at least a portion of the biological activity of the protein with reduced immunogenicity. In addition, the linkage groups formed in the conjugate of this invention through the use of any one of the activated polyethylene glycols of formulae IIA, IIB, or IIB-1 produces a protein conjugate which is not readily susceptible to in vivo hydrolytic cleavage and is not subject to the disadvantages present in PEG protein conjugates of the prior art.

In accordance with this invention, R, R$_1$, R$_2$, R$_3$, R$_4$, R'$_1$, R'$_2$, R'$_3$, and R'$_4$ and R$_5$ can be any lower alkyl, preferably methyl. The term lower alkyl designates lower alkyl groups containing from 1 through 6 carbon atoms, such as methyl, ethyl, n-propyl, isopropyl, etc. Generally the preferred alkyl group is a lower alkyl group containing from 1 to 4 carbon atoms with methyl being most preferable. R$_1$, R$_2$, R$_3$, R$_4$, and R$_5$ can also be hydrogen, but R$_1$, R$_2$, R$_3$ and R$_4$ are not simultaneously hydrogen.

In accordance with this invention, x, y, and z can be selected from any combination of numbers such that the resulting conjugate contains at least a portion of the biological activity of the IFN which forms the conjugate. It is apparent that the sum of x, y, and z, and m is inversely proportional to the amount of biological activity of the IFN which is retained by the conjugate. The numerical value of x, y, and z represent the number of glycol units in the polyglycol which form the conjugate. The term m represents the number of free or accessible amino groups contained by the IFN which can react with the activated PEG mixture. The higher the value of m, and x, y, and z, the higher the molecular weight of the conjugate. In accordance with this invention x, y and z are any number so that molecular weight of the conjugate, excluding the weight of the protein, is between about 300 to about 30,000 daltons. Preferably for IFN, m is a number from 1 through 3. A highly preferred embodiment is a monoPEGylated conjugate where m is 1, produced by conditions such that a high yield is obtained of IFN conjugate composed of IFN where only one free amino group has reacted with the PEG reagent of formula II-A, or II-B, or II-B1. In accordance with a preferred embodiment where m is 1, x, y, and z are any number so that the glycol which forms the conjugate has an average molecular weight of from about 300 to about 30,000 daltons, preferably about 1,000 to about 10,000 daltons, especially about 1,000 to about 5,000 daltons. In a particularly preferred embodiment, the molecular weight is about 2,000 daltons. In one preferred embodiment of the conjugates of formulae IA and IB, x and y are 5 to 500 and z is 0 to 4. In a particularly preferred embodiment, the glycol used is a mixture of glycols wherein x is between 10 to 100, y is between 1 to 10 and z is 0.

When the reagent of any one of formula IIA, II-B, or IIB-1 is reacted with IFN, which contains more than one free amino group, the conjugate may be produced as a mixture of various reaction products of IFN with the PEG-reagent mixtures. These reaction products form as a result of the reaction of the PEG reagent with one or more of the free amino groups. This is signified by m in formula IA and IB. For example, where the IFN contains three free amino groups, the activated PEG reagent can react with one of the free amino groups, with two of the free amino groups or with all three. In this situation the mixture contains conjugated reaction products formed in all three cases. Since the various conjugated reaction products in this mixture have vastly different molecular weights, depending on the value of m, i.e. 1, 2, or 3, these reaction products can be separated by conventional methods such as chromatography. To determine if m, and x, y, and z have been selected properly, the separated conjugated reaction products can be screened for biological activity by the same means used to screen the parent IFN to determine if the conjugated reaction product still retains a portion of the biological activity of the IFN used to form the conjugate. In this manner, the numbers m, and x, y, and z can be adjusted in any desired manner to provide the desired activity.

In accordance with the preferred embodiment, m is 1. Where m is 1, this conjugate can be obtained even when there are two or more free amino groups. The activated PEG reagent will react first with one of the free amino groups contained within the IFN. By regulating the concentration of the reagents such as the IFN, and reaction conditions, in accordance with standard methods of amine condensation, one can regulate the degree of pegylation of the free amino groups contained within the protein. In proteins containing one or more free amino groups, where one of the free amino groups is more reactive than the other amino groups, conditions may be selected so that the protein is reacted with the activated PEG compound to form the compound of formula IA or IB where m is 1. Other free amino groups contained within amino acids which form the protein may be subsequently reacted with the PEG by allowing the condensation reaction to proceed longer or by utilizing other stronger conditions.

Interferon includes all types, for example, $\alpha$, $\beta$ and $\delta$ interferon, and subtypes of these types, for example $\alpha 2A$. Interferon may be obtained from tissues or tissue cultures or may be produced by recombinant techniques. Methods for producing and isolating natural or recombinant interferon are well known in the art.

The advantage of using the reagents of formulae IIA, IIB and IIB-1 where at least one of $R_1$, $R_2$, $R_3$, $R_4$, $R'_1$, $R'_2$, $R'_3$, and $R'_4$ is lower alkyl, in particular methyl (alkyl substituted reagents) lies in an unexpected enhancement of the yield of conjugate, i.e., PEGylated protein, when the alkyl substituted reagents are used as compared to corresponding unsubstituted reagents. Alkyl substituted reagents yield at least twice the amount of conjugates in the same amount of reaction time compared to the corresponding unsubstituted reagents in producing such conjugates.

If administered to patients for therapeutic purposes, the conjugates of formulae IA and IB produced from the above-described substituted reagents would have an unexpectedly enhanced in vivo half-life in the bloodstream of the patient when compared to conjugate formed from corresponding unsubstituted reagents. Although in vivo half-life is directly proportional to the molecular weight of the conjugate, a conjugate produced from a substituted reagent, surprisingly will have as long a half-life as a higher molecular weight conjugate produced from unsubstituted reagent. A longer half-life for a therapeutic agent in a patient's bloodstream provides enhanced efficiency for administering the agent to a patient. For example, conjugates made from alkyl substituted reagents can be administered less frequently and/or in lower amounts than conjugates made from the corresponding unsubstituted reagent. In order to enhance the efficiency of administration of biologically active protein conjugates with polyethylene glycol, increased molecular weights of polyethylene glycol have been used in forming these protein conjugates. However, biological efficacy of the active conjugated IFN diminishes with increasing molecular weight. However, through the use of the conjugates of this invention produced with substituted reagents, efficiency of administration is enhanced over the use of the corresponding unsubstituted conjugate with less increase in molecular weight.

The conjugate of formula I-A is produced as follows:

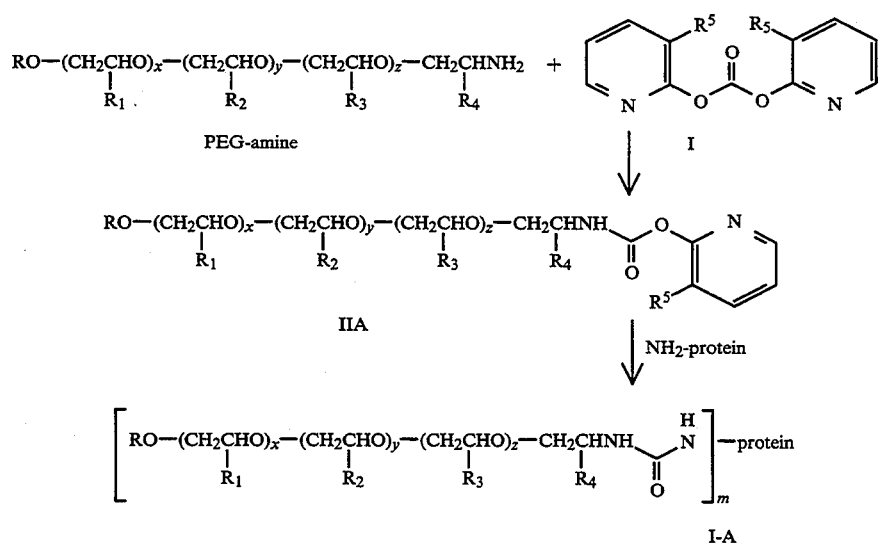

wherein R, $R_1$, $R_2$, $R_3$, $R_4$, and $R_5$, m and x, y, and z are as above; with the proviso that any one or more of $R_1$, $R_2$, $R_3$, $R_4$, and $R_5$ may be lower alkyl.

In this reaction a PEG-amine is mixed with the compound of formula I in a hydrocarbon or chlorinated hydrocarbon solvent to produce the compound of formula IIA. The compound of formula IIA can be condensed in an aqueous medium with one or more of the free amino groups of the protein to produce the conjugate of formula IA. This reaction can be carried out under conventional conditions for condensing amines in an aqueous medium. Generally this reaction is carried out in a standard aqueous buffer solution having a pH of between 7 and 10 to produce the conjugate of formula IA. This reaction may produce a mixture of PEG protein conjugates of various molecular weights depending upon the number of free amino groups within the protein and the time of the reaction. The PEG protein conjugates may then be separated into their individual components by conventional methods such as high performance liquid chromatography (HPLC) or gel electrophoresis. Any conventional conditions for separating compounds by molecular weight with HPLC or gel electrophoresis may be used. Separation of this mixture can be carried out according to molecular weights of the products formed as described herein.

To produce an IFN conjugate of formula IB the following reaction scheme can be used:

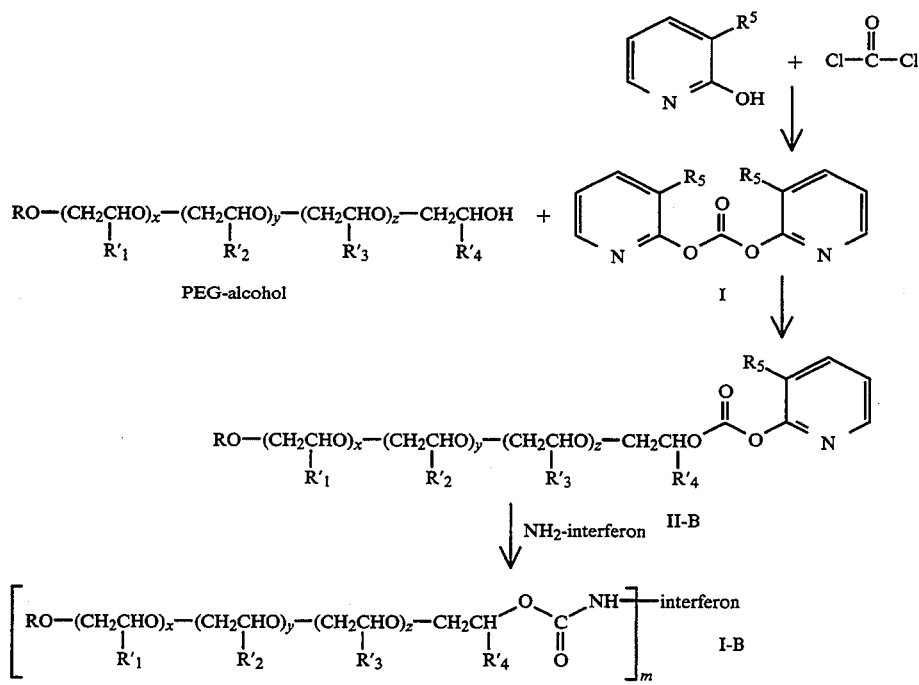

wherein R, R'₁, R'₂, R'₃, R'₄, R₅, m, x, y, and z are as above.

The compound of formula I is produced by condensing phosgene with 2-hydroxypyridine (substituted if R₅=lower alkyl) using any conventional method for condensing an acid halide with an alcohol.

The condensation of a PEG alcohol with the compound of formula I is effected by using conventional conditions for condensing an alcohol with a carbonate to produce the compound of formula II-B. The compound of formula II-B is condensed with the protein through one or more free amino groups on the protein to produce the compound of formula I-B. This reaction is carried out in the manner described for the condensation of the compound of formula IIA to produce the conjugate of formula I-A. Depending upon the number of free amino groups contained within the protein which react with the compound of formula II-B, the conjugate of formula I-B may be formed as a mixture of conjugates having different molecular weights. This conjugate mixture can be separated in the manner described hereinbefore.

The compound of formula IB can also be produced using the following reaction scheme:

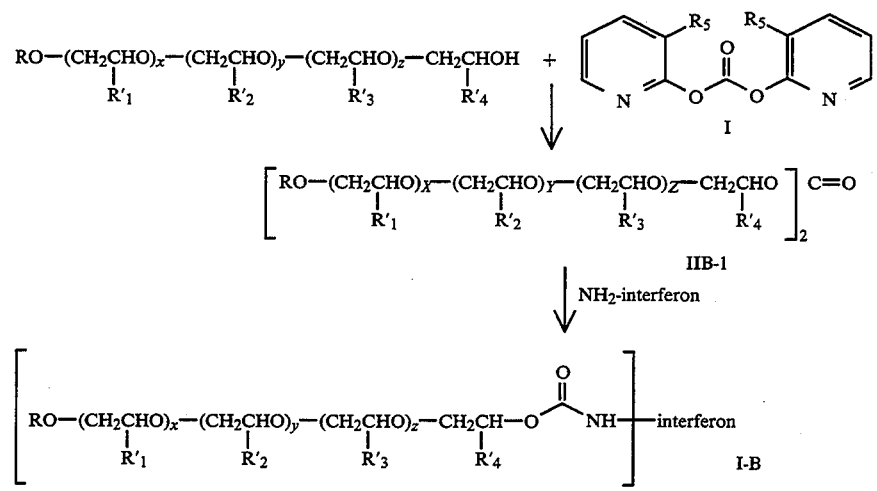

wherein R, R'₁, R'₂, R'₃, R'₄, R₅, m, x, and y are as above. In this reaction scheme, PEG-alcohol is condensed with the compound of formula I to produce the compound of formula IIB-1. In this reaction, the compound of IIB is formed as an intermediate which then reacts with a second mole of PEG-alcohol to produce the compound of formula IIB-1. In carrying out this reaction, the PEG-alcohol is present in at least 2 moles per mole of the compound of formula I. In this procedure any conventional method of condensing an alcohol with a carbonate can be used. The compound of formula IIB-1 is reacted with interferon to form the conjugate of formula I-B in the manner described for the conversion of the compound of formula IIA to the compound of formula IA. Depending upon the amount of free amino groups contained by the protein, condensation of the compound of formula IIB-1 with the protein produces a mixture of conjugates which can be separated into their individual components in the manner hereinbefore described for the separation of the conjugate of formula IA.

This invention is further illustrated by the following examples.

As used in these examples, Jeffamine 2070 is a 2070 average molecular weight monomethoxypolyoxyalkylene propylamine polymer derived from propylene and ethylene oxide which is composed of a polyethylene glycol backbone and contains an average of 30% randomly incorporated propylene oxide groups.

Jeffamine 1000 is a 1000 average molecular weight monomethoxypolyalkylene propylamine polymer derived from propylene and ethylene oxide which is composed of a polyethylene glycol backbone containing 14% of specifically incorporated propylene oxide groups where x is an average of 18.6, y is an average of 1.6, and z is 0 (x, y and z are used here with the same significance as described above).

All reagents described in these examples may be stored dessicated in amber glass at 4° C. until needed. Fresh aliquots are used for each modification.

EXAMPLES

Example 1

Preparation of alpha,alpha-Oxomethylene bi[omega-methoxypoly(oxy-1,2-ethanediyl)]SRU 111

From a suspension of 1.5 g MPEG (methoxypolyethylene glycol) (m.w. −5000) in 80 ml of dry toluene was distilled 50 ml of solvent. The solution was then cooled and 30.5 mg of di-2-pyridylcarbonate added. The resulting mixture was then refluxed for 24 hr. The solution was then cooled and the resulting precipitate filtered and washed with a small volume of toluene followed by diethyl ether. The solid was then dried under high vacuum to give 0.6 g of alpha, alpha'-oxomethylene bis(omega-methoxypoly(oxy-1,2-ethanediyl) SRU 111 as a white powder. PEG-modified interferon was prepared by method 1 described below.

Preparation of PEG-modified Interferon-alpha

Method 1: Recombinant interferon-alpha at 5 mg protein per ml was dialyzed against a buffer containing 5 mM sodium acetate, pH 5.0, 120 mM NaCl. Potassium thiocyanate was added to obtain a final concentration of 0.5M, and the pH adjusted by addition of one-tenth volume of 1M Tricine-sodium hydroxide, pH 11.9, to obtain a final pH 10.0 solution. PEG-reagent was added to the protein at a 3:1 molar ratio from solid or dissolved in DMSO (the volume of DMSO was less than 10% of the total). Modification was allowed to proceed at room temperature for a time from 30 minutes to 4 hours, followed by addition of 1M L-glycine (pH 6.3) to a final concentration of 20 mM to stop further modification. PEG-modified protein was precipitated by addition of 3.5M ammonium sulfate, 50 mM sodium phosphate, pH 7.0, to a final concentration of 1.1M ammonium sulfate (1.0M ammonium sulfate for a PEG-10000), the precipitate collected by centrifugation, washed and redissolved in 25 mM ammonium acetate, pH 5.0. PEG-modified proteins were purified by chromatography on a hydrophobic exchange column (for example 75× 7.5 mm) such as BioRad TSK Phenyl-5-PW or Toyopearl Phenyl-650M, using a gradient of decreasing ammonium sulfate in 50 mM sodium phosphate, pH 7.0. Alternatively, PEG-IFN was purified by gel filtration on a Sephacryl S-200 column (for example a 90 cm. ×3.2 cm. column) (Pharmacia) that was equilibrated in 25 mM sodium acetate (pH 5.0), 200 mM NaCl. PEG-modified protein was identified by SDS-PAGE. Protein eluted from the column corresponding to interferon having one ($PEG_1$-IFN)or two ($PEG_2$-IFN) bound PEG were pooled, concentrated and protein determined by absorbance at 280 nm or by colorimetric assay (Pierce). PEG-IFN was stored at 4° C. in buffer containing 50 mM sodium phosphate, pH 7.0, 0.3M ammonium sulfate.

Method 2: Interferon $\alpha$-2$a$ at a protein concentration of approximately 6 mg per mL, was dialyzed into 5 mM sodium acetate, pH 5.0, 0.12M sodium chloride. The protein concentration was determined by measuring the absorbance at 280 nm using 1.0 mg$^{-1}$ mL as the extinction coefficient. The protein solution was mixed with the modifying reagent at a 1:3 molar ratio of protein to reagent. The modification reaction was initiated by adjusting the pH to 10.0 using one-tenth volume of 0.1M $Na_2B_4O_7$—NaOH, pH 10.7. Following incubation at room temperature for one hour, the reaction was stopped by addition of one-twentieth volume of 1M glycine, pH 7.5. After 3–5 minutes, the pH was decreased to 5.0–6.0 by addition of one-twentieth volume of 1M sodium acetate, pH 4.0.

The solution containing PEG-interferon, quenched reagent and unmodified interferon was diluted four-fold with 40 mM ammonium acetate, pH 4.5, and loaded onto a CM-cellulose column (Whatman CM-52, approximately 0.5 ml resin per mg protein). After washing the column by 5 volumes of 40 mM ammonium acetate, pH 4.5, PEG-interferon and unmodified interferon were eluted using a linear sodium chloride gradient (0–0.5M) in the 40 mM ammonium acetate pH 4.5. Fractions containing protein were identified by absorbance at 280 nm, and PEG-interferon containing fractions were identified by SDS-PAGE.

PEG-interferon was further purified by size exclusion-gel filtration chromatography on a column containing Sephacryl S-200 resin (Pharmacia LKB). Fractions eluted from the column were analyzed by SDS-PAGE and the peak material containing PEG-interferon pooled.

EXAMPLE 2

Preparation of alpha,alpha-Oxomethylene bis[omega-methoxypoly(oxy-1,2-ethanediyl)]SRU 28.3

By the procedure described in Example 1, MPEG (m.w. 1300) was converted to alpha,alpha-oxomethylene bis[omega-methoxypoly(oxy-1,2-ethanediyl) SRU 28.3, and PEG-modified interferon was prepared using this reagent by method 1 described in Example 1.

EXAMPLE 3

Preparation of alpha-Methyl-omega-[2[[(2-Pyridinyloxy)carbonyl]oxy]-ethoxy]-poly-(oxy-1,2-ethanediyl) SRU 111.7

From a solution of 1 g MPEG molecular weight 5000 dissolved in 30 ml of dry $CH_2Cl_2$ was distilled 10 ml of solvent. The solution was cooled to room temperature and 132 mg (0.6 mM) of di-2-pyridyl carbonate and 4 mg of DMAP were added. The resulting solution was then stirred for 14 hours and the solvent removed under vacuum. The residue was triturated with diethyl ether and the resulting precipitate filtered. The product was then dissolved in 7 ml of dry glyme, warmed to cause dissolution, and the resulting solution allowed to cool and stand at room temperature for several hours. The resulting precipitate was then filtered and washed with 2×5 ml of dry glyme. The solid was then dried in a vacuum oven and under a stream of nitrogen to give 0.7 g of alpha-[(2-pyridinyloxy)carbonyl]omega-methoxypoly(oxy-1,2-ethanediyl) SRU 111.7.

Anal. Calcd for $C_9H_{11}NO_4(CH_2CH_2O)_{111.7}$: C,54.57; H,9.02; N,0.28. Found: C,54.51; H,9.19; N, 0.28.

PEG-modified interferon was prepared using this reagent by method 1 described in Example 1.

EXAMPLE 4

Preparation of alpha-[(2-Pyridinyloxy)carbonyl]omega-methoxypoly(oxy-1,2-ethanediyl) SRU 225

By the procedure described in Example 3, MPEG molecular weight 10,000 was converted to alpha-[(2-pyridinyloxy)carbonyl]omega-methoxypoly(oxy-1,2-ethanediyl), SRU 225.

Anal, Calcd for $C_9H_{11}NO_4(CH_2CH_2O)_{225}$: C,54.54; H,9.08; N,0.14. Found: C,54.54; H,9.12; N,0.11.

PEG-modified interferon was prepared using this reagent by method 1 described in Example 1.

EXAMPLE 5

Preparation of alpha-Methyl-omega-[2-[2-[[2-pyridinyloxy)carbonyl]oxy]-propoxy]propoxy poly(oxy-1,2-ethanediyl) SRU 64.7

From a solution of 0.5 g of alpha-2-[2-(hydroxypropoxy)propyl]-omega-methoxypoly(oxy-1,2-ethanediyl) SRU 64.7 in 40 ml of dry $CH_2Cl_2$ was distilled 15 ml of solvent. To the solution was then added 108 mg of di-2-pyridyl carbonate, 4 mg of DMAP and several beads of 4 A molecular sieve. The mixture was then stirred overnight, filtered and the solvent was then removed under reduced pressure. The residue was purified by means of size exclusion chromatograph. PEG-modified interferon was prepared using this reagent by method 1 described in Example 1.

EXAMPLE 6

Preparation of alpha-Methyl-omega-[2-[2-[[(2-pyridinloxy)carbonyl]oxy]-propoxy]propoxy]poly(oxy-1,2-ethanediyl) SRU 110

By the procedure described in Example 5, alpha-2-[2-(hydroxypropoxy)propyl]-omega-methoxypoly(oxy-1,2-ethanediyl) SRU 110, was converted to alpha-methyl-omega-[2-[2-[[(2-pyridinyloxy)carbonyl]oxy]propoxy]propoxy]poly(oxy-1,2-ethanediyl) SRU 110. PEG-modified interferon was prepared using this reagent by method 1 described in Example 1.

EXAMPLE 7

Preparation of Methyloxirane, polymer with oxirane, [2- [[(2-pyridinyloxy)-carbonyl]amino]propyl methyl ether (MO/O=10/32)

From a solution of 1 g of Jeffamine M-2070 (Texaco Chemical Co.) in 40 ml of dry $CH_2Cl_2$ was distilled 15 ml of solvent. The solution was cooled to 0° C. and 215 mg of di-2-pyridyl carbonate was added. The resulting solution was stirred for an additional 4 hr at 0° C. after which time the solvent was removed under reduced pressure. The residue was then purified by means of two size exclusion columns attached in sequence (500 Å and 1000 Å). The product shows two bands in the UV at 232 nm and 310 nm. PEG-modified interferon was prepared using this reagent by method 2 described in Example 1.

EXAMPLE 8

Preparation of Methyloxirane, polymer with oxirane, [2-[[(3-methyl-2-pyridinyloxy)carbonyl]amino]propyl methyl ether (MO/O=10/32)

By the procedure described in Example 7, 1 g of Jeffamine M-2070 was reacted with bis(3-methyl-2-pyridyl)carbonate to give methyloxirane, polymer with oxirane, [2-[[(3-methyl-2-pyridinyloxy) carbonyl]amino]propyl methyl ether (MO/O=10/32). PEG-modified interferon was prepared using this reagent by method 1 described in Example 1.

EXAMPLE 9

Preparation of Methyloxirane, polymer with oxirane, [2-[[2-pyridinyloxy)-carbonyl]amino]propyl methyl ether, block (MO/O=1.6/18.6)

By the procedure described in Example 7, 0.6 g of Jeffamine M-1000 (Texaco Chemical Co.) was reacted with 155.6 mg of di-2-pyridyl carbonate to give methyloxirane, polymer with oxirane, [2[[(2-pyridinyloxy)carbonyl]amino]propyl methyl ether, block (MO/O=1.6/18.6). PEG-modified interferon was prepared using this reagent by method 1 described in Example 1.

Antiviral activity of interferon: Antiviral activity of interferon and PEG-modified interferon was determined (Rubenstein, et al., (1981) J. Virol. 37: 755–758; Familletti, et al., (1981) Methods Enzymol. 78: 387–394). All assays were standardized relative to control. The interferon standard used in the assay had specific activity of $2 \times 10^8$ units per mg of protein.

Conditions used for modification of interferon were based on optimized protocols as described. PEG-modification was analyzed by SDS-PAGE for conversion of interferon to monoPEG-interferon over various times of incubation (chemical reactivity), and for distribution into different species of PEG-interferon conjugates (site selectivity). In SDS-PAGE, PEG-modified species were observed as slower migrating bands on the gel. Both monoPEG and diPEG-interferons were produced in sufficient yield so that these species could be purified from the reaction mixtures by hydrophobic interaction chromatography. Purified PEG-interferons were tested for antiviral activity and compared with unmodified interferon-α2a standards. The molecular weights of the polymers used as well as the antiviral activity of some of the pegylated derivatives are described in Table 1.

TABLE 1

| Physical Properties of PEG Reagents and Biological Activities of their Protein Conjugates | | |
|---|---|---|
| | | Antiviral Activity (% control) |
| Compound of Example: | Polymer mol/Wt. | monoPEG | diPEG |
| 4 | 10000 | 25 | 2 |
| 3 | 5000 | 40 | 4 |
| 1 | 5000 | 40 | ND |
| 6 | 5000 | 40 | ND |
| 5 | 3000 | 60 | ND |
| 7 | 2200 | 45 | ND |

TABLE 1-continued

Physical Properties of PEG Reagents and Biological Activities of their Protein Conjugates

| Compound of Example: | Polymer mol/Wt. | Antiviral Activity (% control) | |
|---|---|---|---|
| | | monoPEG | diPEG |
| 2 | 1300 | 70 | ND |
| 9 | 1100 | 100 | 40 |

ND = not determined

We claim:

1. A physiologically active interferon conjugate having the formula:

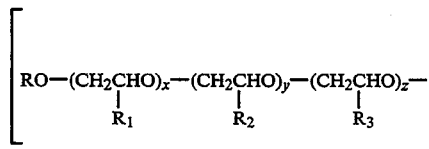

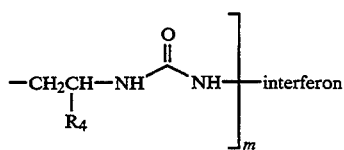

wherein R is lower alkyl; $R_1$, $R_2$, $R_3$, and $R_4$ are H or lower alkyl; m is a number up to the number of accessible amino groups in the protein; and x, y and z are selected from any combination of numbers such that the conjugate has at least a portion of the biological activity of the interferons which forms the conjugate, with the proviso that at least one of $R_1$, $R_2$, $R_3$, and $R_4$ is lower alkyl.

2. The interferon conjugate of claim 1 wherein x, y, and z are selected such that the molecular weight of the conjugate minus the molecular weight of the interferon is about 300 daltons to about 30,000 daltons.

3. The interferon conjugate of claim 1 wherein m is 1.

4. The interferon conjugate of claim 1 wherein R is methyl.

5. The interferon conjugate of claim 2 wherein x, y, and z are selected such that the molecular weight of the conjugate minus the molecular weight of the interferon is about 1,000 daltons to about 5,000 daltons.

6. The interferon conjugate of claim 5 wherein x, y, and z are selected such that the molecular weight of the conjugate minus the molecular weight of the interferon is about 2,000 daltons.

7. The interferon conjugate of claim 1 wherein x and y are 5.0 to 500.0 and z is 0.0 to 4.0.

8. The interferon conjugate of claim 2 wherein x is 10.0 to 100.0, y is 1.0 to 10.0, and z is 0.

9. The interferon conjugate of claim 5 wherein the interferon is interferon α2A.

10. The interferon conjugate of claim 2 wherein m is 1.

11. An interferon conjugate of claim 10 wherein R, $R_2$, and $R_4$ are $CH_3$; $R_1$ is H; x is 18.6, y is 1.6, and z is 0.

12. A reagent of the formula:

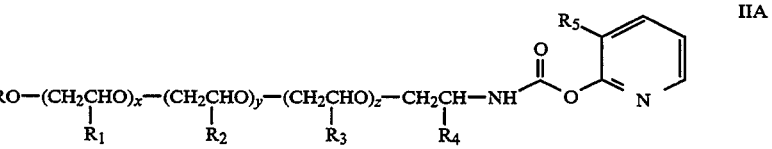

wherein R is lower alkyl, $R_1$, $R_2$, $R_3$, $R_4$, and $R_5$ are H or lower alkyl; and x, y, and z are selected from any combination of numbers such that the reagent when conjugated to a protein allows said protein to retain an activity at least equivalent to a portion of its biological activity when not conjugated, with the proviso that at least one of $R_1$, $R_2$, $R_3$, and $R_4$ is lower alkyl.

13. A reagent of claim 12 wherein x, y and z are selected such that the molecular weight of said reagent is about 300 daltons to about 30,000 daltons.

14. A reagent of claim 12 wherein R is methyl.

15. A reagent of claim 12 wherein x is 10.0 to 100.0, y is 1.0 to 10.0, and z is 0.0 to 4.0.

16. A reagent of the formula:

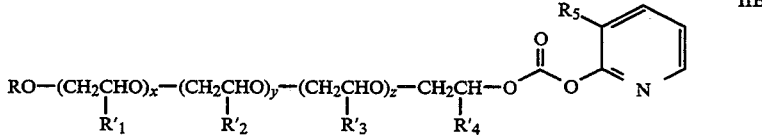

wherein R is lower alkyl; $R'_1$, $R'_2$, $R'_3$, $R'_4$, are H or methyl; $R_5$ is H or lower alkyl; and x, y, and z are selected from any combination of numbers such that the reagent when conjugated to a protein allows said protein to retain an activity at least equivalent to its biological activity when not conjugated.

17. A reagent of claim 16 wherein x, y and z are selected such that the molecular weight of said reagent is about 300 daltons to about 30,000 daltons.

18. A reagent of claim 16 wherein any one or more of $R_1'$, $R_2'$, $R_3'$ and $R_4'$ is methyl.

19. A reagent of claim 16 wherein R is methyl.

20. A reagent of claim 16 wherein x is 10.0 to 100.0, y is 1.0 to 10.0 and z is 0.0 to 4.0.

* * * * *